United States Patent [19]
Burns

[11] Patent Number: 5,232,111
[45] Date of Patent: Aug. 3, 1993

[54] STOPPER-SHIELD COMBINATION CLOSURE

[75] Inventor: James A. Burns, Elizabeth, N.J.

[73] Assignee: Becton, Dickinson and Company, Franklin Lakes, N.J.

[21] Appl. No.: 6,157

[22] Filed: Jan. 19, 1993

Related U.S. Application Data

[63] Continuation of Ser. No. 923,012, Jul. 30, 1992, abandoned, which is a continuation of Ser. No. 700,665, May 13, 1991, abandoned.

[51] Int. Cl.⁵ .................... B65D 41/28; B65D 39/00
[52] U.S. Cl. .................. 215/320; 215/247; 215/296; 215/364; 215/DIG. 3; 604/403
[58] Field of Search ............. 215/320, 247, 248, 249, 215/296, 356, 364, DIG. 3; 604/192, 403, 416; 128/763, 764

[56] References Cited

U.S. PATENT DOCUMENTS

| | | | |
|---|---|---|---|
| 2,964,208 | 12/1960 | Heyl et al. | 215/40 |
| 3,128,896 | 4/1964 | Schnier | 215/364 |
| 3,460,702 | 8/1969 | Andrews | 215/37 |
| 3,779,415 | 12/1973 | Eddleman et al. | 215/364 X |
| 3,854,617 | 12/1974 | Edwards | 215/364 |
| 4,186,840 | 2/1980 | Percarpio | 215/247 |
| 4,187,952 | 2/1980 | Percarpio | 215/247 |
| 4,204,606 | 5/1980 | Micheli | 215/307 |
| 4,355,111 | 10/1982 | Shimizu et al. | 215/248 X |
| 4,416,661 | 11/1983 | Norman et al. | 215/247 X |
| 4,456,138 | 6/1984 | Bereziat | 215/232 |
| 4,465,200 | 8/1984 | Percarpio | 215/247 |
| 4,573,602 | 3/1986 | Goldberg | 215/256 |
| 4,637,520 | 1/1987 | Alvi | 215/320 |
| 4,765,379 | 8/1988 | Szymanski | 215/228 X |
| 4,869,384 | 9/1989 | Ogle, II | 215/247 |
| 4,967,919 | 11/1990 | Earhart | 215/247 |

FOREIGN PATENT DOCUMENTS

| | | |
|---|---|---|
| 0028411 | 5/1981 | European Pat. Off. |
| 0102851 | 3/1984 | European Pat. Off. |
| 0189153 | 7/1986 | European Pat. Off. |
| 7338759 | 5/1975 | France ............... 215/320 |
| 2422569 | 11/1979 | France . |
| 527140 | 9/1939 | United Kingdom . |
| 2020252 | 11/1979 | United Kingdom . |

Primary Examiner—Allan N. Shoap
Assistant Examiner—Vanessa Caretto
Attorney, Agent, or Firm—Alan W. Fiedler; Robert P. Grindle

[57] ABSTRACT

A combination closure is provided, particularly for evacuated collection tubes for body fluids such as blood, including an elastomer stopper and plastic cover combination with cooperating locking surfaces spaced around the circumference thereof. The stopper includes vertically spaced sealing rings for insertion into the open end of the tube. Also, the stopper includes a plurality of circumferentially spaced protrusions and the cover or shield cooperating circumferentially spaced indentations or ports to provide a locking force between the protrusions and indentations. As a result, the dimensions of the stopper and the plastic cover are reduced, which in turn reduces the penetration force required to insert a needle through the stopper. Moreover, the reduced dimension of the closure allows it to be locked to a bead on the tube whether plastic or glass, and the lesser overall diameter allows the closure on the tube to fit more tube holders or containers during and prior to use. In addition, the smaller dimension reduces the tendency of the closure to "rock" on the tube. The closure of the invention includes means for containing liquid droplets or aerosol when the needle is removed from the stopper.

13 Claims, 5 Drawing Sheets

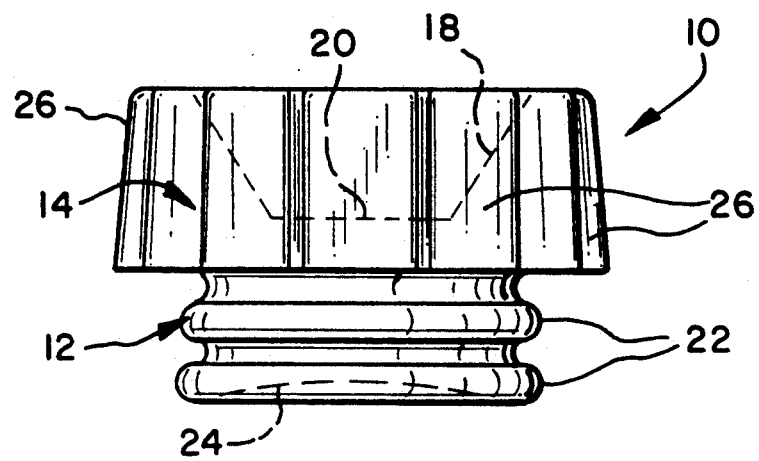
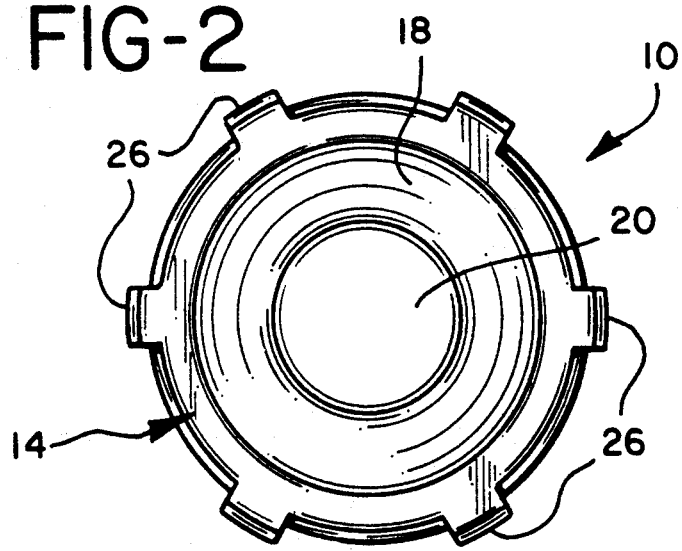

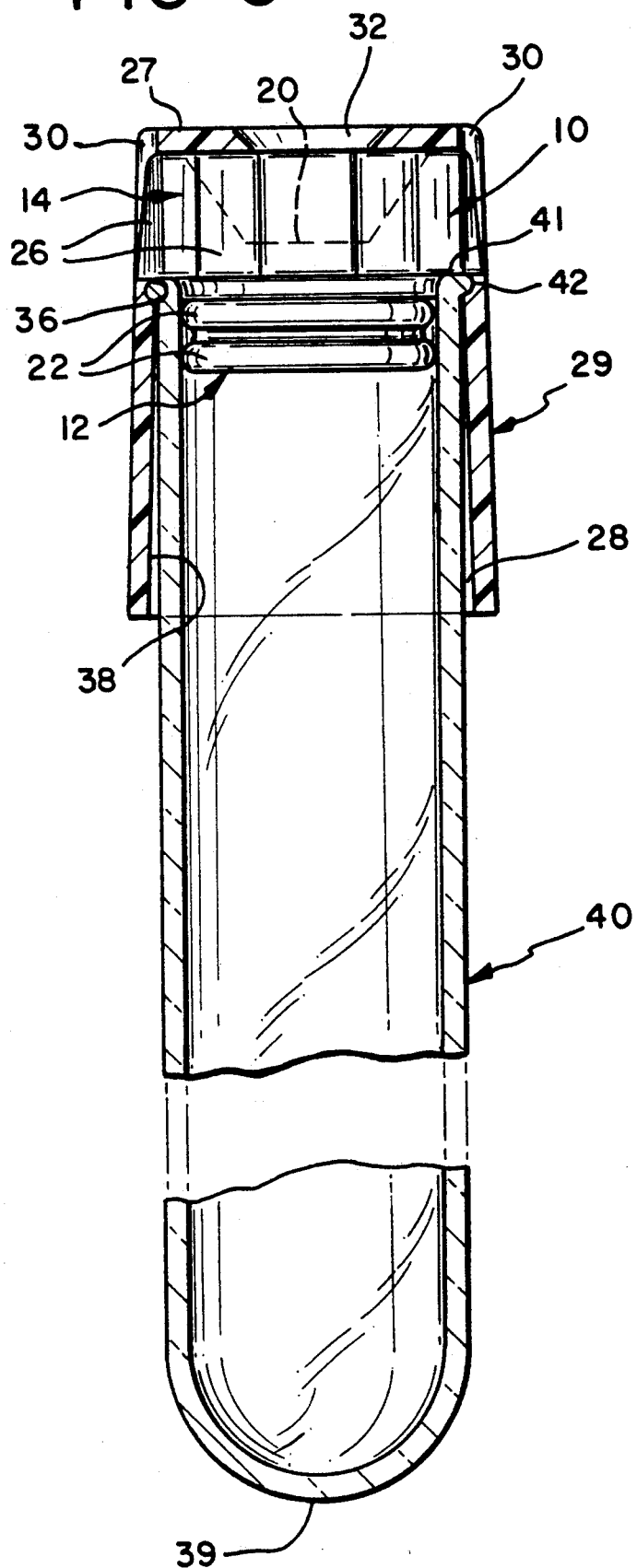

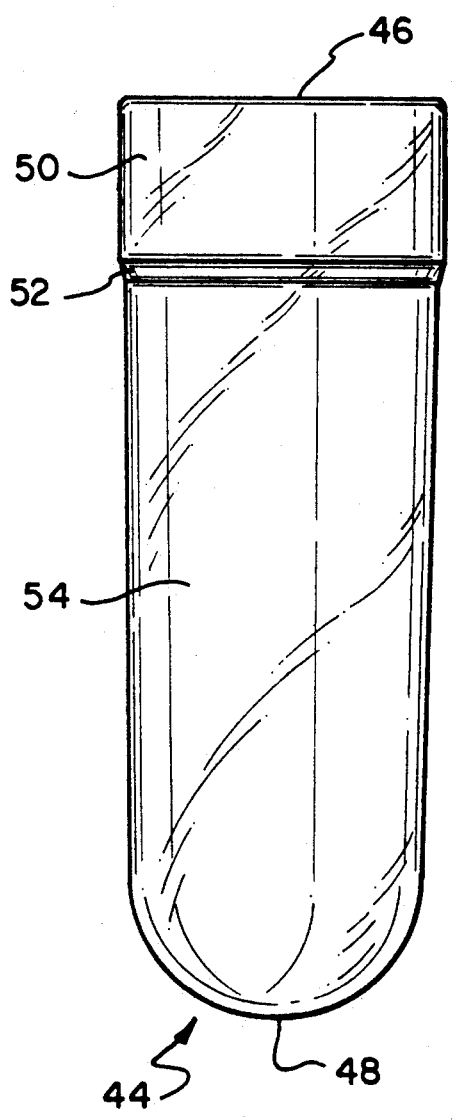
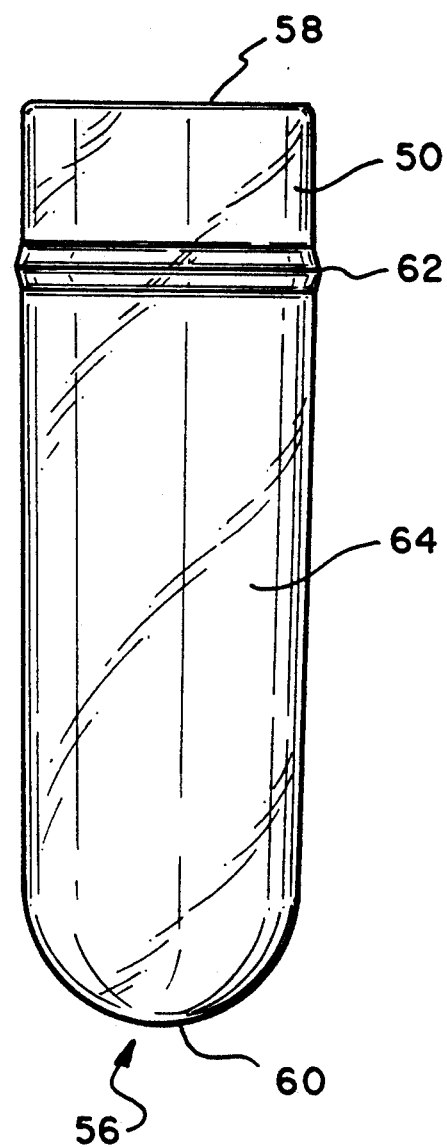

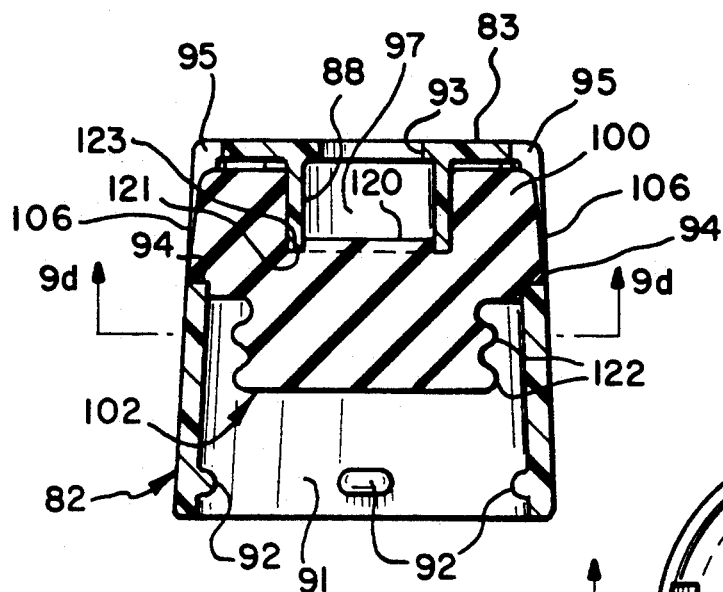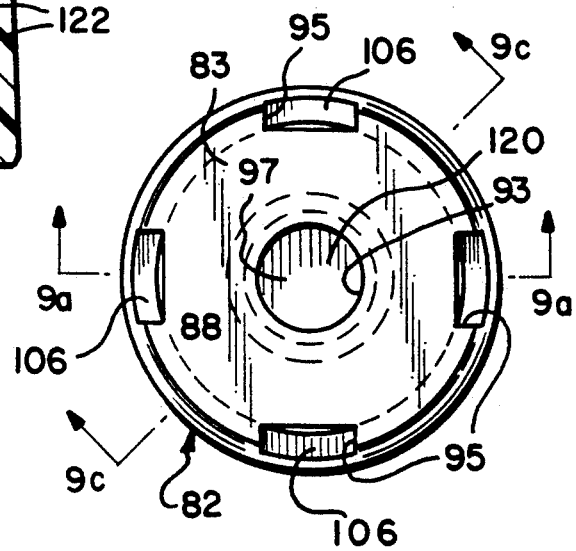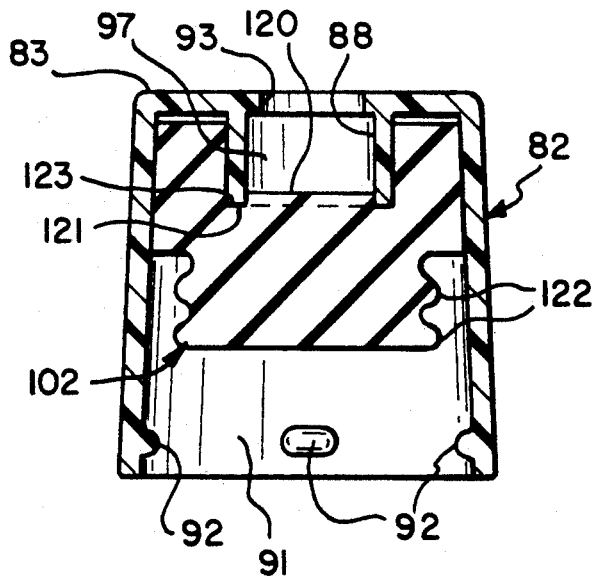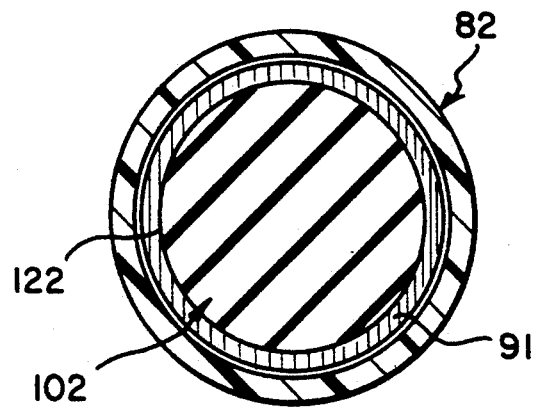

STOPPER-SHIELD COMBINATION CLOSURE

This is a continuation of copending U.S. patent application Ser. No. 07/923,012, filed on Jul. 30, 1992, now abandoned which is a continuation of U.S. patent application Ser. No. 07/700,665, filed on May 13, 1991, which is now abandoned.

BACKGROUND AND DESCRIPTION OF THE INVENTION

This invention relates to devices for taking samples of body fluids from patients for subsequent examination in a clinical lab. More particularly, this invention relates to a specific configuration of evacuated tube with the vacuum in the tube being utilized to draw body fluid specimens from the body of a patient by a phlebotomist, nurse or doctor.

As practitioners in the art of blood draw procedures understand, it is most important that the vacuum in evacuated tubes utilized for that purpose be maintained at the proper level during storage for subsequent use. That is, these practitioners, during use of such evacuated tubes, insert one end of a double ended needle into the vein of a patient. The other end extends through an open ended holder for receiving, sequentially, a plurality of evacuated tubes. It is most important that this procedure be carried out efficiently and as rapidly as possible, as anyone will understand, since the technician or phlebotomist carrying out the procedure must contend with a patient having a needle stuck through their skin into a vein. If, for example, the vacuum is deficient in one tube during such a procedure, it entails subsequent removal of the tube and insertion of another tube which prolongs the unpleasant procedure involved.

This invention is directed particularly to a stopper-shield combination for sealing the open end of such body fluid collection tubes. That is, the tube, regardless of its make up or nature, must maintain the vacuum therein by a specific closure for that purpose. If the closure is defective or does not provide appropriate seal, the vacuum property deteriorates over time.

As a further consideration for the combination stopper-plastic cover or shield combinations currently utilized for body fluid collection tubes of the kind discussed herein, it is most important during subsequent examination, where samples of the material are being removed from the tubes that the insertion of a needle through the stopper for such withdrawal is relatively easily carried out. That is, if great effort is required to force a needle through the stopper, then the clinician in the laboratory may get involved with accidents wherein blood contamination may take place. Or simply the routine insertion of a great many needles through a great many stoppers entails more effort than should be required.

It is to this kind of situation that the present invention is directed. That is, this invention is directed to a specific configuration of elastomer stopper for sealing the closed end of an evacuated body fluid collection tube with a plastic shield or cover positioned thereover. It is routine to utilize a plastic shield over the elastomer stopper for several reasons. First, the plastic shield provides a gripping surface for easy removal of the elastomer stopper from the evacuated tube to overcome the force of the vacuum, and for removal of samples, as required in the laboratory. Moreover, if samples are to be removed by a needle, as discussed above, when the needle is removed, blood droplets may form on the top surface of the elastomer stopper. The shield provides an overhang over the top surface to contain any of these blood droplets or an aerosol of the liquid spurting out of the top of the stopper when the needle is being withdrawn.

Efforts have been made in the past to develop stopper plastic shield combinations for alleviating some of the problems discussed above. One such device is disclosed and claimed in U.S. Pat. No. 4,465,200, which covers a stopper-plastic shield combination with cooperating annular abutments so that the plastic shield easily lifts the stopper from the top of an evacuated tube. Moreover, this particular configuration includes an overhang of the plastic shield over the top surface of the rubber stopper to prevent exposure to blood droplets withdrawn with the withdrawal of a needle from the stopper. While the structure is successful in providing the characteristics desired, the configuration of stopper and shield provided with that combination is somewhat cumbersome in size and requires a substantial space for storing such tubes before and after use.

Other representative patents directed to problems of the kind discussed above include U.S. Pat. Nos. 4,187,952 and 4,186,840 which are both directed to combination peelable seal arrangements and plastic caps over the top of elastomer stoppers for the purpose of preserving the sterility thereof prior to use.

Further representative combination closures of the kind discussed herein include U.S. Pat. Nos. 3,460,702, 4,204,608; European Patent Publication No. 0102851 and European Patent Publication No. 0028411.

With this invention by contrast, a specific configuration of stopper plastic shield or cover combination is provided in which the specific configuration allows for dimensional reduction in the overall size of the closure. This allows for readily reduced storage space for such blood collection tubes both prior and after use.

Moreover, the combination closure of the invention herein reduces the stresses placed on the elastomer stopper, once it is inserted into the body fluid collection tube. Because of this, the user may use substantially less force to insert a needle through the elastomer stopper. As discussed above, this has the effect of reducing the overall effort in a daily environment handling many such tubes and inserting needles through the stoppers, but also it reduces the possibility of accidents simply because of the ease of insertion and withdrawal allowed with the invention here.

The results of this stopper-shield combination of the invention is achieved because the lower insertion portion of the stopper includes a plurality of vertically spaced alternating indentations and rings. The vertically spaced sealing rings inserted into the upper end of the tube provide spaced areas of sealing, while reducing the internal stresses in the stopper body.

Moreover, the upper flange of the stopper which extends out over the top of the tube of interest includes a plurality of circumferentially spaced protrusions. These protrusions cooperate with a plurality of ports or indentations in the plastic shield utilized with the stopper. By doing so, a proper positive connection is achieved between the plastic shield or cover and the related stopper while reducing the overall dimensions of the combination. The upper over-hang portion of the stopper is inserted in the plastic shield and twisted. This causes the protrusions on the stopper to move into place in the shield wall.

With the foregoing and additional objects in view, this invention will now be described in more detail, and other objects and advantages thereof will be apparent from the following description, the accompanying drawings, and the appended claims.

DESCRIPTION OF THE DRAWINGS

FIG. 1 is a side elevational view of the stopper of the invention illustrating the vertically spaced sealing rings on the lower portion of the stopper, and the circumferentially spaced protrusions on the upper portion of the stopper;

FIG. 2 is a top plan view of the stopper of FIG. 1;

FIG. 6 is a longitudinal sectional view of the closure device of the invention positioned on the top of a glass tube, and showing the cooperating position of the closure combination of the invention with the annular glazed bead positioned at the top of the glass tube;

FIGS. 7 and 8 are side elevational views of representative plastic tubes which may be utilized with a specific embodiment of closure of the invention; and FIGS. 9a, 9b, 9c and 9d show various views of the plastic shield stopper combination utilized for closing plastic tubes for body fluid collection, and showing a specific embodiment of the invention with an annular sealing ring positioned adjacent the top well of the elastomer stopper to contain blood droplets or aerosol upon removal of a needle from insertion through the elastomer stopper.

Referring to the drawings in which like reference characters refer to like parts throughout the several views thereof, in FIG. 1 the stopper of the invention generally designated 10 is shown. Stopper 10 includes a depending annular portion 12 with a plurality of vertically spaced sealing rings 22 which cooperate with the annular internal surface at the top portion of a tube for maintaining the vacuum in the tube. The upper annular flange portion 14 of stopper 10 includes a plurality of circumferentially spaced protrusions 26, which cooperate with ports or indentations in the plastic shield or cover for the stopper, which will be discussed below. The stopper 10 includes an upper well portion having walls 18 which converge into an upper surface 20 for receiving the point of a needle inserted through stopper 10. The lower surface of stopper 10 includes a well 24 shown in section. FIG. 2 shows a top plan view of the stopper 10 and shows the positioning of the locking protrusions 26.

Referring now to FIGS. 3, 4 and 5 a stopper 10 is shown positioned for insertion in the direction of arrow 25 into its cooperating plastic cover or shield 29. As can be seen in FIGS. 3 and 4, shield 29 includes an upper opening 32 to allow access of the user to the top surface 20 of stopper 10 once the stopper is inserted into the shield and the stopper-shield combination are positioned on the top of an evacuated tube.

Figure 5:
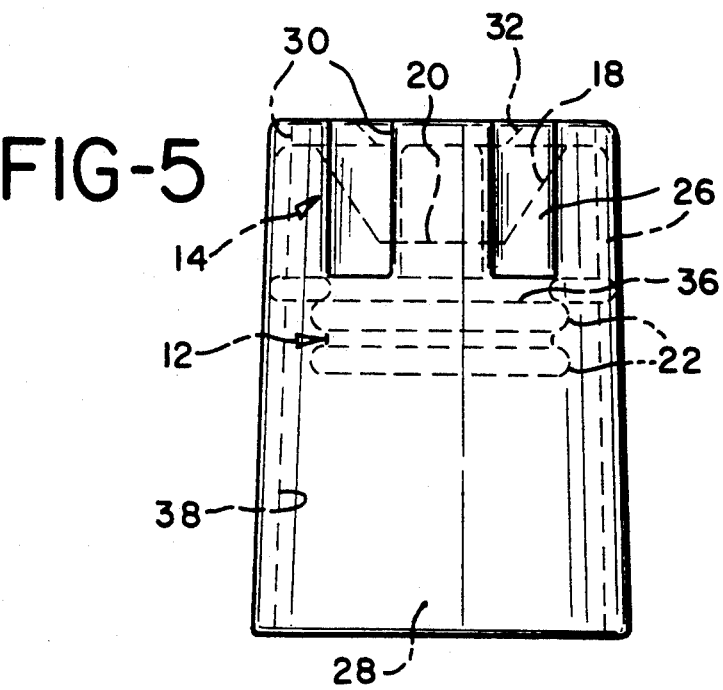
FIG. 5 is a side elevational view, similar to that of FIG. 3, but with the stopper inserted fully into the shield of the invention for subsequent mounting on a tube.

Plastic shield 29 includes an internal annular wall 38 defining a chamber 28 for receiving the inserted stopper 10 which is shown in its final position in shield 29 in FIG. 5. Once this has taken place, then, when a tube is inserted into the internal chamber 28 of shield 29, the annular bead of a glass tube, for example, cooperates with the annular undercut 36 positioned in annular wall 38 of the plastic shield 29.

Figure 3:
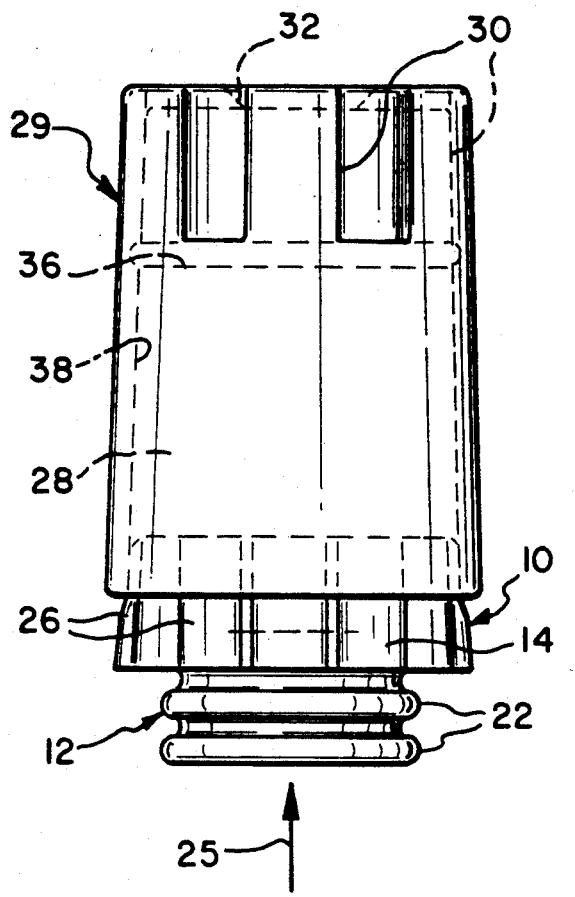
FIG. 3 is a side elevational view of the plastic shield stopper combination of the invention with the initial insertion of the stopper into the plastic shield.
Figure 4:
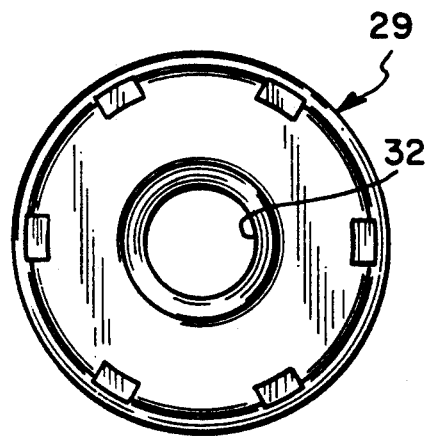
FIG. 4 is a top plan view of the device of FIG. 3.

As can be seen in the top plan view shown in FIG. 4, the plastic shield or cover 29 includes a plurality of circumferentially spaced ports 30 for receiving the cooperating protrusions 26 of stopper 10. As mentioned above, this is done by inserting stopper 10 in shield 29 and twisting to cause protrusions 26 to move into ports or openings 30. Thus, the two parts are joined together circumferentially so that when the user wishes to remove the stopper from the tube, any force applied circumferentially to the plastic shield readily moves the elastomer stopper from gripping the internal surface of the glass tube, for example.

FIG. 6 shows the closure combination of the invention positioned on a glass tube 40. The entire assembly is shown in section, and tube 40 is a conventional evacuated glass tube having a closed end 39 and an open end 41 sealed by the stopper 10 of the invention. The tube 40 includes an annular glazed bead 42 for cooperating with the undercut 36 positioned on the internal surface of the plastic shield 29, as shown in FIG. 6. As can be readily seen in FIG. 6, the top surface 27 of plastic shield 29 includes opening 32 for gaining access by needle into the top surface 20 of elastomeric stopper 10.

For the purpose of collecting body fluid specimens, it has been conventional for many years to utilize glass tubes for this purpose, because glass provides appropriate maintenance of a vacuum in the tubes for a practical shelf-life prior to use of such tubes for blood collection, for example. As mentioned above, it is most important for the user at the moment when a blood collection procedure is taking place, for example, to have the vacuum be appropriate for carrying out the procedure.

However, in recent years, plastic tubes have been developed and are being further developed routinely. The reason for this is that plastic tubes, as will be understood by anyone, will not break when dropped. This eliminates one problem with blood contamination, which is most important these days with the development of AIDS. Moreover, since such tubes, once a body fluid specimen is collected in the tubes, are inserted in centrifuge devices for application of high speed centrifugal force, the tubes sometimes break under those conditions splattering blood over clinical lab technicians. Plastic tubes, again, remove substantially such dangers.

Thus, FIGS. 7 and 8 are representative of configurations of plastic tubes developed recently. They include tube 44 in FIG. 7 and tube 56 in FIG. 8. Both include upper collars such as 50 shown in FIG. 7 with an annular transition abutment 52 between the upper collar portion 50 of the tube 44 and the lower tube portion 54 thereof. Of course, both tubes 44 and 56 include closed ends 48 and 60, respectively. Also, they include open ends 46, 58, respectively, for closure by an elastomer stopper-plastic cover or shield combination of the invention. As can be seen in FIG. 8, the annular transition abutment 62 is configured differently than the annular transition abutment 52 in FIG. 7. For this reason, it is necessary to configure the internal surface of the stopper-shield combination of the invention to cooperate with these different configurations. Also, walls 64 of tube 56 are more tapered in tube 56.

Referring now to FIGS. 9a, 9b, 9c and 9d, an embodiment of the invention is shown in section of a stopper-plastic shield combination for positioning on the top of a plastic evacuated tube. As shown in FIG. 9a, stopper 102 is shown with the lower sealing portion thereof having the vertically spaced rings 122. The upper portion 100 of stopper 102 includes a plurality of circumferentially spaced apart protrusions 106, which in this case number 4 rather than the 6 in stopper 10. Plastic shield 82 has an internal annular compartment or chamber 91 for receiving and inserting therein stopper 102 and the upper portion of a plastic tube. The plurality of circumferentially spaced protuberances 92 cooperate with the annular transition abutments 52, 62 of the plastic tube embodiments shown in FIGS. 7 and 8.

The combination shown in section in FIG. 9a includes an annular cooperating sealing surface 94 between an edge of a portion of the annular plastic shield 82 and the upper portion 100 of the stopper 102. The plastic shield, in this embodiment includes an annular sealing ring 88 positioned to depend from the opening 93 in the top surface 83 of plastic shield 82. The lower end 121 of ring 88 is inserted into an annular groove 123 in stopper 102 to provide a cooperating sealing surface between stopper 102 and plastic shield 82 in the vicinity of the well 97 where blood droplets may form on the surface 120, when a needle is withdrawn from stopper 102.

The various showings in FIG. 9 with the section lines show the various cooperating surfaces of the stopper 102 and shield 82 of the embodiment of this invention for use with plastic tubes, in particular. As can be seen in FIG. 9b, for example, a top plan view indicates the cooperation of the circumferentially spaced openings 95 in shield 82 for receiving the circumferentially spaced protrusions 106 of elastomer stopper 102.

As can be seen in FIG. 9a, however, this sectional view shows the discontinuity of the cooperating protrusions 106 and ports or openings 95. This also provides the viewer with the showing of the reduced dimensional characteristics of the combination claimed. The sectional views shown in FIG. 9d show the positioning of the cooperating chamber 91 for receiving the top edge of an evacuated tube when the stopper plastic shield combination is positioned on the top of such a tube.

Thus, there is provided, in accordance with this invention, a new composite closure assembly for evacuated tubes for taking body fluid samples and especially blood samples. The closure assembly is more hygienic to the user and the patient in that lower contamination from blood is provided by the assembly thus reducing exposure of a technician to aerosol caused by either stopper removal from the top of an evacuated tube or removing the needle after insertion through the stopper of the combination claimed. Moreover, because of the relative ease with which the user may insert and remove a needle because of the vastly reduced internal stresses of the combination claimed herein for sealing an evacuated tube, the exposure of the type discussed herein is reduced simply because there is much less likelihood of accidents involved simply because the applied force is so much less.

Of course, as users will understand, this substantial reduction in required force for insertion and removal of a needle through the elastomer stopper relieves the technician of a substantial amount of work during the course of a work day. Finally, because of the substantially reduced dimensional characteristics of the combination, the closure and its accompanying tube take up much less space for storage prior to use and during and after use. Moreover, the sealing assembly herein is more readily removable from an evacuated tube because it provides a cooperating gripping surface while the reduced internal stresses of the stopper inserted into the top of the tube makes it much easier to remove the assembly from the evacuated tube.

As is apparent from the foregoing, the arrangements of apparatus provided in accordance herewith are readily and simply manufactured by mass production techniques and conventional molding procedures, and the parts may be simply assembled and mounted on evacuated tubes with a limited amount of effort.

While the apparatus herein disclosed forms preferred embodiments of this invention, this invention is not limited to these specific forms of apparatus, and changes can be made therein without departing from the scope of this invention which is defined in the appended claims.

What is claimed is:

1. An assembly for closing evacuatable tubes for receiving samples of body fluids, said assembly comprising:
    an annular stopper body;
    said stopper body having an upper annular flange portion with a top surface and a lower annular portion, with both said upper and lower annular portions being integral with each other;
    said lower portion having a vertical surface comprised of a plurality of vertically spaced integral annular rings;
    a plurality of protrusions circumferentially spaced around said upper annular flange portion;
    an annular shield body having an annular wall defining a chamber for receiving said stopper body;
    said shield body having a top surface with a central opening for receiving a needle therethrough; and
    a plurality of openings through said wall of said shield body positioned so that each opening receives one of said plurality of protrusions on said stopper body when said stopper body is received in said shield chamber.

2. The assembly of claim 1, further comprising:
    a well in the top surface of said upper annular flange portion of said stopper body;
    said well having a bottom surface for receiving the needle through said stopper body; and
    said well formed from walls extending from the top surface of said stopper body to the bottom surface of said well.

3. The assembly of claim 2, wherein said central opening in said shield top surface has a diameter that is less than a diameter of said well so that said shield top surface provides an annular overhang around said well.

4. The assembly of claim 1, wherein said lower annular portion of said stopper body is received in an open end of an evacuatable tube in sealing engagement with the open end.

5. The assembly of claim 1, further comprising:
    an annular integral sealing ring on said shield body;
    said sealing ring coaxial with said shield body and extending from said shield top surface to surround said central opening in said shield top surface; and
    an annular groove in said stopper body for receiving said sealing ring.

6. An assembly for closing evacuatable tubes for receiving samples of body fluids, said assembly comprising:
    an annular stopper body;

said stopper body having an upper annular flange portion and a lower annular portion, with both said upper and lower annular portions being integral with each other;

said lower portion having a surface comprised of a plurality of vertically spaced integral annular rings;

a plurality of protrusions circumferentially spaced around said upper annular flange portion;

an annular shield body having an annular wall defining a chamber for receiving said stopper body;

said shield body having an internal surface and a top surface with a central opening for receiving a needle therethrough;

a plurality of openings through said wall of said shield body positioned so that each opening receives one of said plurality of protrusions on said stopper body when said stopper body is received in said shield chamber; and an annular undercut in the internal surface of said shield body.

7. The assembly of claim 6, further comprising:
an elongated evacuatable glass tube having a closed end and an open end; and
an annular bead positioned on a rim of said open end of said glass tube,
wherein said lower annular portion of said stopper body is received in said open end of said evacuatable tube in sealing engagement with said open end said annular bead is received in said undercut.

8. An assembly for closing evacuatable tubes for receiving samples of body fluids, said assembly comprising:
an annular stopper body;
said stopper body having an upper annular flange portion and a lower annular portion, with both said upper and lower annular portions being integral with each other;
said lower portion having a surface comprised of a plurality of vertically spaced integral annular rings;
a plurality of protrusions circumferentially spaced around said upper annular flange portion;
an annular shield body having an annular wall defining a chamber for receiving said stopper body;
said shield body having an internal surface and a top surface with a central opening for receiving a needle therethrough;
a plurality of openings through said wall of said shield body positioned so that each opening receives one of said plurality of protrusions on said stopper body when said stopper body is received in said shield chamber; and
a plurality of circumferentially spaced protuberances on the internal surface of said shield body.

9. The assembly of claim 8, further comprising:
an elongated evacuatable plastic tube;
said plastic tube having an open end and a closed end;
an integral annular collar formed adjacent said open end of said plastic tube; and
an annular transition abutment on said plastic tube for engaging said circumferentially spaced protuberances on the internal surface of said shield body when said plastic tube is positioned in said shield chamber.

10. An assembly for closing evacuatable tubes for receiving samples of body fluids, said assembly comprising:
an annular stopper body;
said stopper body having an upper annular flange portion with a top surface and a lower annular portion, with both said upper and lower annular portions being integral with each other;
said lower portion having a surface comprised of a plurality of vertically spaced integral annular rings;
a plurality of protrusions circumferentially spaced around said upper annular flange portion;
an annular shield body having an annular wall defining a chamber for receiving said stopper body;
said shield body having an internal surface and a top surface with a central opening for receiving a needle therethrough;
a plurality of openings through said wall of said shield body positioned so that each opening receives one of said plurality of protrusions on said stopper body when said stopper body is received in said shield chamber;
a plurality of circumferentially spaced protuberances on the internal surface of said shield body;
a well in the top surface of said upper annular flange portion of said stopper body;
said well having a bottom surface for receiving the needle through said stopper body;
said well formed from walls extending from the top surface of said stopper body to the bottom surface of said well;
an annular integral sealing ring on said shield body;
said sealing ring coaxial with said shield body and extending from said shield top surface to surround said central opening in said shield top surface; and
an annular groove in said stopper body for receiving said sealing ring.

11. The assembly of claim 10, further comprising:
an elongated evacuatable plastic tube;
said plastic tube having an open end and a closed end;
an integral annular collar formed adjacent said open end of said plastic tube; and
an annular transition abutment on said plastic tube for engaging said circumferentially spaced protuberances on the internal surface of said shield body when said plastic tube is positioned in said shield chamber.

12. An assembly for closing evacuatable tubes for receiving samples of body fluids, said assembly comprising:
an annular stopper body having an upper annular flange portion;
a plurality of protrusions circumferentially spaced around said upper annular flange portion;
an annular shield body having an annular wall defining a chamber for receiving said stopper body;
said shield body having a top surface with an opening for receiving a needle therethrough; and
a plurality of openings through said wall of said shield body positioned so that each opening receives one of said plurality of protrusions on said stopper body when said stopper body is received in said shield chamber.

13. The assembly of claim 12, further comprising:
an annular integral sealing ring on said shield body;
said ring coaxially with said shield body and extending from said shield top surface to surround said opening in said shield top surface; and
an annular groove in said stopper body for receiving said sealing ring.

* * * * *